(12) United States Patent
Abe

(10) Patent No.: US 6,532,825 B1
(45) Date of Patent: Mar. 18, 2003

(54) FATIGUE DAMAGE DETECTION SENSOR FOR STRUCTURAL MATERIALS AND MOUNTING METHOD THEREOF

(75) Inventor: Makoto Abe, Isumi-gun (JP)

(73) Assignee: BMC Co., LTD, Chiba (JP)

( * ) Notice: Subject to any disclaimer, the term of this patent is extended or adjusted under 35 U.S.C. 154(b) by 0 days.

(21) Appl. No.: 09/581,323

(22) PCT Filed: Sep. 24, 1999

(86) PCT No.: PCT/JP99/05218

§ 371 (c)(1),
(2), (4) Date: Jul. 24, 2000

(87) PCT Pub. No.: WO00/19183

PCT Pub. Date: Apr. 6, 2000

(30) Foreign Application Priority Data

Sep. 28, 1998 (JP) .......................................... 10/288699

(51) Int. Cl.$^7$ .............................................. G01N 19/00
(52) U.S. Cl. .............................. 73/804; 73/799; 73/808; 73/845
(58) Field of Search ........................ 73/767, 799, 787, 73/762, 808, 803, 804, 845

(56) References Cited

U.S. PATENT DOCUMENTS

| | | | | |
|---|---|---|---|---|
| 3,979,949 A | * | 9/1976 | Smith ............................ | 73/787 |
| 4,502,337 A | * | 3/1985 | Archer .......................... | 73/762 |
| 4,916,954 A | * | 4/1990 | Buzzard ........................ | 73/799 |
| 5,014,544 A | * | 5/1991 | West ............................. | 73/40.7 |
| 5,520,055 A | * | 5/1996 | Fussinger ..................... | 73/762 |
| 5,528,151 A | * | 6/1996 | Perez ........................... | 324/525 |
| 5,614,680 A | * | 3/1997 | Fussinger ..................... | 73/799 |

* cited by examiner

*Primary Examiner*—Max Noori
*Assistant Examiner*—Andre Allen
(74) *Attorney, Agent, or Firm*—Stetina Brunda Garred & Brucker

(57) ABSTRACT

Focusing on the application of a predetermined relationship between the length of a fatigue damage detection sensor having a width of a specified shape and a required sensitivity or sensing accuracy (crack propagation rate), the present invention provides a fatigue damage detection sensor for structural materials and mounting method thereof, wherein when the length between a pair of fixing portions for fixing to a surface of a structural material M, both ends of a sensor body (2) sandwiching a notched portion (5) is defined as 2H, the length of a crack C that can propagate from a tip (5A) of the notched portion (5) is defined as (a), the number of times that a working load acts on the material is defined as N, and the crack propagation rate is defined as da/dN, the length 2H between said fixing portions is set so as to obtain a required sensitivity with which da/dN is proportional to $H^{0.5m}$ (m is a constant determined by a material). According to this fatigue damage detection sensor for structural materials and mounting method thereof, the sensor can provide a high sensing performance to stably and reliably determine the level of fatigue damage caused to a structural material, based on the rate and amount of crack propagation.

11 Claims, 13 Drawing Sheets

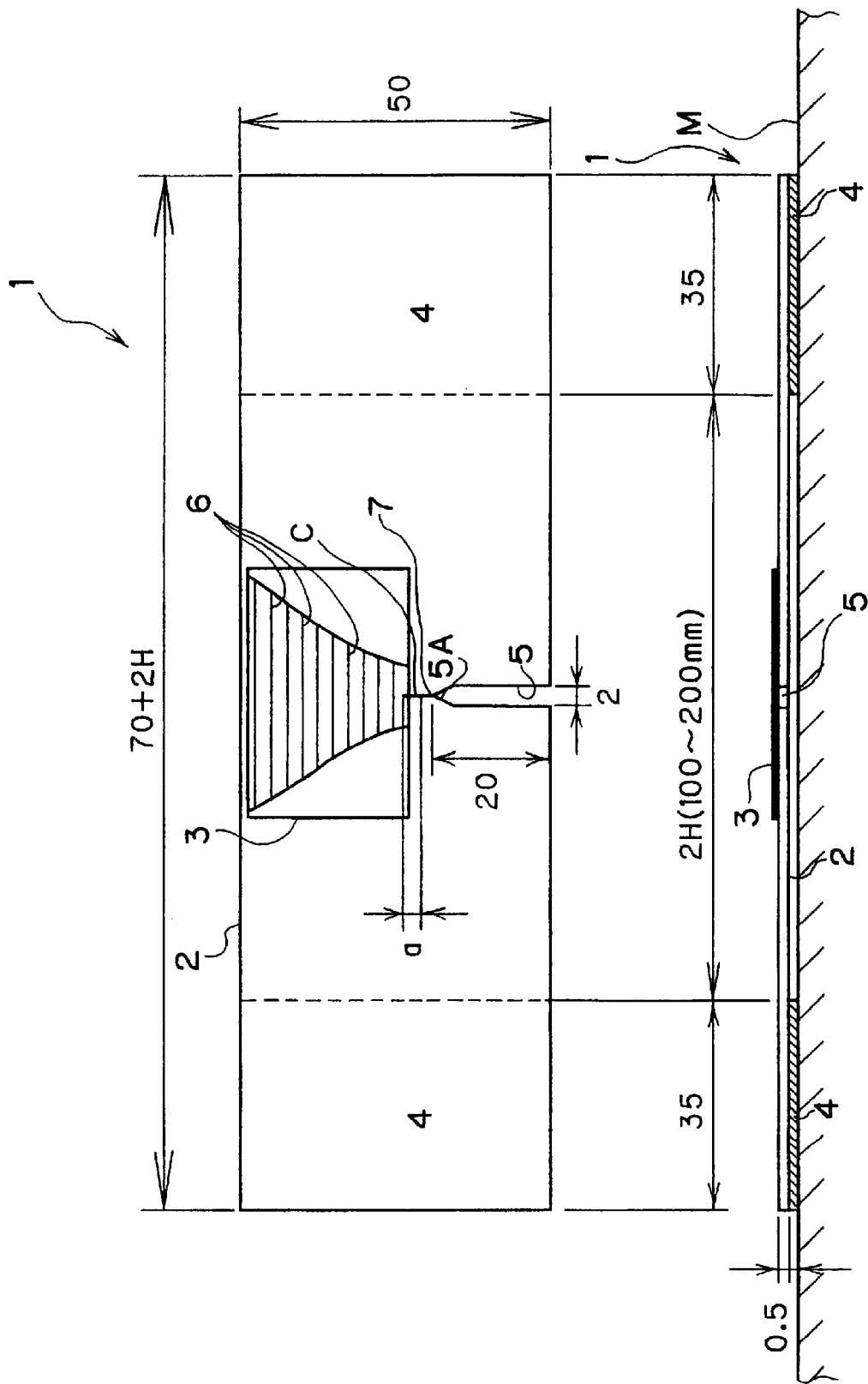

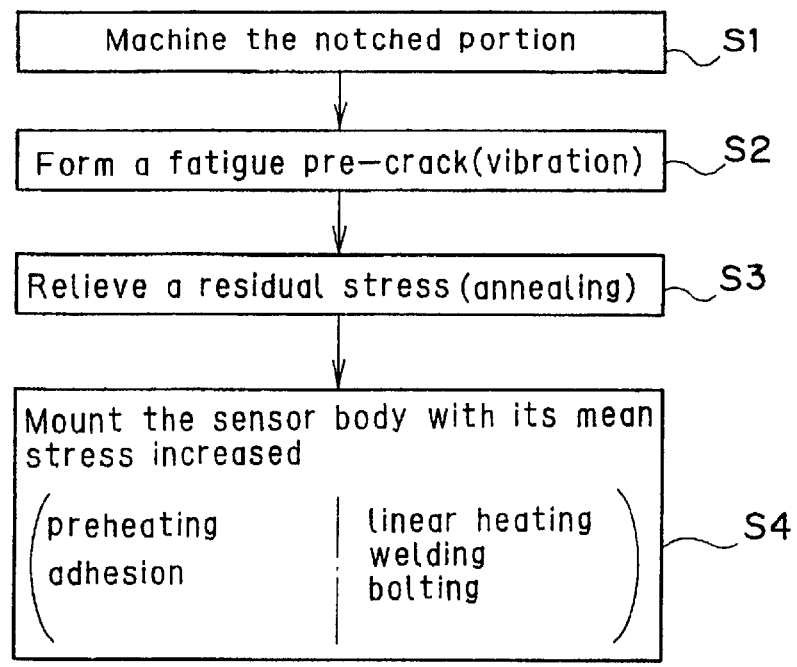
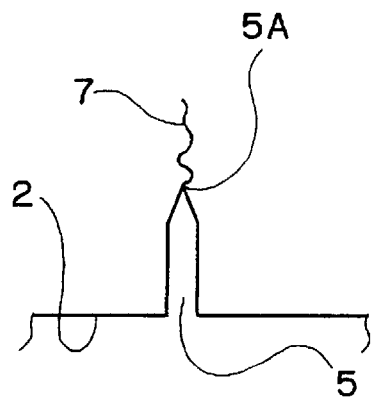

-○- R=0.8
-△- R=0.67
-▽- R=0.5
-□- R=0.33
-◇- R=0.1

(black→no propagation)

× no propagation
△ low propagation
○ stable propagation

△ low propagation
○ stable propagation

Fig.22 stress range on sensor, $\Delta\sigma$(MPa)

- ○ confirmation test (GL=100mm)
- ● confirmation test (GL=200mm)

JSSC mean curve
$da/dN = 1.5 \times 10^{-11}(\Delta K^{2.75} - 2.9^{2.75})$ fatigue crack propagation rate, $da/dN$(m/cycle) vs stress intensity factor range, $\Delta K$(MPa$\sqrt{m}$)

Fig.23 stress range, $\Delta\sigma$(MPa) vs number of cycles, $N$(cycles)

a=1mm, a=10mm

JSSC D, JSSC E, JSSC F, JSSC G

FATIGUE DAMAGE DETECTION SENSOR FOR STRUCTURAL MATERIALS AND MOUNTING METHOD THEREOF

TECHNICAL FIELD

The present invention relates to a fatigue damage detection sensor for structural materials and mounting method thereof, and in particular, to a fatigue damage detection sensor for structural materials that senses the history of stress and the level of fatigue damage caused to various structural materials or members (base materials) such as steel materials which are used to build structures such as bridges, iron towers, and other buildings as well as machine structures such as construction machines, to mounting method thereof capable of accurately and reliably mounting the fatigue damage detection sensor so as to provide a predetermined sensitivity.

BACKGROUND ART

Conventional structural materials may be fatigue-damaged under a working load, and it is essential to periodically inspect these materials to maintain safety.

These structural materials, however, not only have a large number of inspection items to be constantly checked but also require expertise and experience for visual inspections, scaffolding for inspections that is required due to a possible danger involved in these operations, a large amount of time for inspections, and the continuance of inspections over a long time period. Thus, there is a need to accurately and efficiently carry out determination of the fatigue damage condition of these materials and sensing of abnormality.

In such inspections or maintenance and management, sensing of fatigue damage is divided into three historical stages including a first stage in which no crack has not occurred despite an accumulated fatigue, a second stage in which damage has occurred as a crack due to the fatigue, and a third stage in which the fatigue has occurred to propagate the crack.

In each of these stages, for example, the first stage requires the level of fatigue accumulation to be determined to sense the possibility of the occurrence of a fatigue crack, the second stage requires a generated crack to be sensed, and the third stage requires the current propagation of a crack to be determined to predict future propagation and a point of time at which the material may be destroyed.

However, the history of stress that may cause a crack was conventionally determined by checking the design and measuring stress over a specified time period. This determination, however, has been inaccurate and has required a large amount of time and costs. That is, there has not been a practical sensor for sensing not only the occurrence but also the propagation of a crack or a method for reliably mounting a detection sensor with a predetermined sensing accuracy and low costs.

DISCLOSURE OF THE INVENTION

The present invention has been achieved in view of these problems, and its object is to provide a fatigue damage detection sensor for structural materials and mounting method thereof wherein the fatigue damage detection sensor can be stably reliably mounted on the material so as to provide a good sensing performance.

Furthermore, another object of this invention is to provide a fatigue damage detection sensor for structural materials and mounting method thereof wherein the sensor can be mounted with a predetermined accuracy so as to sense the occurrence and propagation of a crack appropriately.

Yet another object of this invention is to provide a fatigue damage detection sensor for structural materials and mounting method thereof wherein the sensor allows a crack to be stably generated and propagated on behalf of the structural material without being affected by external environments such as the temperature and humidity so as to predict the level of fatigue damage caused to the structural material based on the rate or amount of propagation.

That is, the present invention focuses on a predetermined relationship between the length of the fatigue damage detection sensor and a required sensitivity or sensing accuracy (crack propagation rate) and attempts to increase the mean stress beforehand by applying this relationship, forming a fatigue pre-crack in the fatigue damage detection sensor beforehand, leveling or relieving a residual stress, and applying an initial stress prior to mounting. A first invention is a fatigue damage detection sensor for structural materials for sensing the stress history of a structural material that is subjected to a working load as well as the level of fatigue damage caused to the material, characterized in that the sensor comprises a detection sensor body configured by a rectangular panel-shaped member that can be mounted on a surface of the structural material and that has a specified width and a predetermined length, the detection sensor body including a notched portion on one or both length-wise sides thereof or inside the plate-shaped member; and a crack detection means located in front of the tip of the notched portion and provided in the sensor body and in that when the length between a pair of fixing portions for fixing to the surface of the structural material, both ends of the sensor body sandwiching the notched portion is defined as 2H, the length of a crack that can propagate from the tip of the notched portion is defined as (a), the number of times that a working load acts on the material is defined as N, and the crack propagation rate is defined as da/dN, the length 2H between the fixing portions is set so as to obtain a required sensitivity with which da/dN is proportional to $H^{1.5}$.

The above described notched portion has a fatigue pre-crack formed at its tip, and a residual stress is relieved from the fatigue pre-crack to increase the mean stress before the sensor body is mounted on the structural material.

A second invention is a method for mounting a fatigue damage detection sensor for structural materials for sensing the level of fatigue damage caused to a structural material that is subjected to an external stress, characterized by comprising the notched portion formation step of forming a notched portion on one or both length-wise sides of a sensor body configured by a rectangular panel-shaped member that can be mounted on the surface of the structural material and that has a specified width and a predetermined length or forming the notched portion inside the panel-shaped member; the fatigue pre-crack formation step of forming a fatigue pre-crack in the notched portion, the residual-stress relief step of relieving the residual stress resulting from the fatigue pre-crack formation step, and the sensor mounting step of mounting the sensor body on the structural material with the mean stress of the sensor body increased.

In the sensor mounting step, the detection sensor body, which has been heated, can be mounted on the structural material.

This pre-heating operation causes the detection sensor body to be contracted when cooled to increase its mean stress due to a difference in temperature and thermal expansion between the sensor body and the structural material.

An appropriate difference in temperature between the detection sensor body and the structural material caused by pre-heating has been found to be about 10° C. or higher, preferably about 30° C.

In the sensor mounting step, the sensor body can be linearly heated while being mounted on the structural material.

This linear heating can also increase the mean stress as in the preheating operation.

Means for mounting the detection sensor body on the structural material may be arbitrary and include adhesion, welding, and bolting, but an adhesion means is preferable due to the easiness of this operation.

Although a step is required that mounts the crack detection means on the detection sensor body in front of the tip of the notched portion, this step may be executed before or after machining the notched portion in the sensor body.

The crack detection means must only be able to detect a crack and may include a crack gauge, an optical crack detection apparatus, or a crack detection apparatus using ultrasonic waves.

In a fatigue damage detection sensor for structural materials and mounting method thereof according to this invention, the detection sensor body with the notched portion formed therein and the crack detection means can be used to detect fatigue damage caused to the structural material with a predetermined sensitivity or detection accuracy, and the sensor can be mounted so as to execute sensing with a stable sensitivity.

In particular, based on the proportionality of the crack propagation rate da/dN to $H^{1.5}$, the fatigue damage detection sensor according to this first invention can adjust the crack propagation rate da/dN to control a required sensitivity. Thus, by setting the lateral length (in a strain (displacement) constraining method for fixing both ends of the sensor body to the surface of the structural material, the length between the pair of fixing portions) of the sensor body at a predetermined value, the sensor body can be mounted with a desired sensitivity.

In the method for mounting a fatigue damage detection sensor according to this second invention, the fatigue pre-crack is formed in the notched portion of the sensor body beforehand, a residual stress generated during the formation of the fatigue pre-crack is relieved, and the mean stress is increased before mounting the sensor body. These apparatuses can ensure that a crack stably occurs and propagates without being affected by external environments such as the temperature and humidity, thereby enabling the history of stress or accumulated fatigue of the structural material to be sensed with practical construction costs and workability using the sensor with the notched portion formed therein.

Even if an actual stress caused by a working load is small, the increased mean stress allows a crack to occur and propagate, and the propagation rate of a crack linearly varies relative to the stress intensity factor range ΔK proportional to $H^{0.5}$, thereby enabling sensing with a predetermined accuracy.

A desirable mean stress corresponds to a tensile stress of stress ratio 0.6 or more. In addition, by allowing the tensile stress to remain, sensing is possible even in a compressed field of the structural material.

In this way, when a working load acting on a structural material of a bridge or the like causes a crack to propagate up to a predetermined threshold, this can be visually confirmed or electrically detected using a crack gauge or a crack detection gauge or apparatus for an alarm or further detailed inspections.

That is, when simply affixed to a structural material, the fatigue damage detection sensor according to this invention can detect the history of stress (history of the magnitude of stress and of the number of stress cycles) acting on the structural material and record the accumulated history of stress so that these records can be used to determine the stress or fatigue accumulated during an arbitrary period in order to predict fatigue damage that may be caused to the structural material.

Next, a fatigue damage detection sensor 1 for structural materials and mounting method thereof according to an embodiment of this invention will be described with reference to FIGS. 1 to 9.

FIG. 1 is a top and front views of the fatigue damage detection sensor comprising an indicator plate 2 (a sensor body), a crack gauge 3 that is an example of a crack detection means, and a lateral pair of affixed portions 4 (fixing portions). In the figure, an example of the size of each part is described in the unit of mm.

The indicator plate 2 constitutes the body of the fatigue damage detection sensor 1, is shaped like a rectangle having a specified width and a predetermined length, and has a generally long V-shaped notched portion 5 on one side.

The crack gauge 3 is placed so as to be opposed to a tip 5A of the notched portion 5 so that stress is concentrated at the tip 5A to allow a crack to occur in the indicator 2 sufficiently earlier than in a base material M when loaded.

The notched portion 5 need not be formed at the center of the indicator plate 2. It may be formed on both sides of the indicator plate 2 or inside the plate.

The crack gauge 3 preferably determines the length of a crack in the indicator plate 2 more easily when placed perpendicularly to the propagation direction of a crack propagating from the tip 5A, and may be a strain gauge 6 or a parallel arrangement of electric resistance wires. A fatigue crack is formed at an end of the tip 5A beforehand, as described below in FIGS. 2 and 3.

The lateral pair of affixed portions 4 are used to fixedly mount the fatigue damage detection sensor 1 on the base material M over a predetermined area. The fatigue damage detection sensor 1 and the base material M are integrated together at the affixed portions 4, and the length of part of the fatigue damage detection sensor 1 located between the affixed portions 4 independently of the base material M is defined as 2H.

The material of the indicator plate 2 and an adhesion for the affixed portions 4 affixed to the base material M may be arbitrary but desirably have durability and a weather resistance and allow the correlationship with stress acting on the base material M and the crack gauge 3 to be stably determined. In general, the adhesion can be thermally set and the indicator plate 2 is formed as thin as possible.

For example, the indicator plate 2 has a thickness of 1 mm or less and a width varying depending on the length of the sensor. If 2H is set at 100 to 200 mm, the width is 10 to 100 mm.

The length of the indicator plate 2 is determined based on a sensitivity required of the damage fatigue sensor 1.

As shown in FIG. 1, when the length of a crack C that can propagate from the tip 5A of the notched portion 5 is defined as (a), the number of times that a working load acts on the material, and the crack propagation rate is defined as da/dN, da/dN is proportional to $H^{1.5}$. Thus, the length 2H between the affixed portions 4 is set so as to obtain a predetermined sensitivity.

That is, when both ends (affixed portions 4) of the fatigue damage detection sensor 1 are fixed and a specified strain $\epsilon$ is applied to these ends and if the modulus of longitudinal elasticity is defined as E, the stress intensity factor K of the tip of the crack C is expressed as follows:

$$K = E \cdot \epsilon \cdot H^{0.5}$$

When the fatigue damage detection sensor 1 is affixed to the base material M having a strain variation range $\Delta K$, the stress intensity factor range $\Delta K$ is expressed as follows:

$$\Delta K = E \cdot \Delta \epsilon \cdot H^{0.5}$$

The crack propagation rate da/dN is proportional to about the third power of $\Delta K$, so it is proportional to $H^{1.5}$.

FIG. 2 is a flowchart showing a procedure for mounting the fatigue damage detection sensor 1. First, the notched portion is machined (step S1).

No fatigue crack occurs in the machined notched portion 5 under such a low stress as generated in the base material M that is an actual structural material or a long time period is required before a crack occurs in this portion.

Thus, a fatigue pre-crack 7 (see the enlarged view in FIG. 3) is formed at step S2.

FIG. 4 is a schematic explanatory drawing of a fatigue pre-crack generator 8 for forming the fatigue pre-crack. The fatigue pre-crack generator 8 comprises a frame 9, a pair of fatigue damage detection sensor grabbing portions 10, and a fatigue pre-crack monitoring sensor 11 wherein the fatigue damage detection sensor grabbing portions 10 are vibrated at predetermined cycles to generate the fatigue pre-crack 7 in the notched portion 5 of the fatigue damage detection sensor 1.

Since the stress used to generate the fatigue pre-crack 7 is set higher than a stress normally occurring in the structural material, the crack C may not propagate stably due to a residual stress generated at the tip of the fatigue pre-crack 7.

Thus, the fatigue damage detection sensor 1 with the fatigue pre-crack 7 formed therein is annealed to relieve the residual stress at step S3 (FIG. 2).

FIG. 5 is a schematic explanatory drawing describing this annealing operation in brief. The fatigue damage detection sensor is accommodated in a heating furnace 12 and heated therein at a predetermined temperature for a predetermined time period. The fatigue damage detection sensor 1 is then left and the furnace is cooled for annealing to relieve the residual stress generated due to the formation of the fatigue pre-crack 7.

Returning to FIG. 2, the fatigue damage detection sensor 1 with its mean stress increased is mounted on the base material M at step S4.

That is, since a repeated stress that may occur in a normal base material M is not so high, the fatigue crack C may not propagate stably in the fatigue damage detection sensor 1. The fatigue stress C has been confirmed to propagate stably even under s low stress if the mean stress of the fatigue damage detection sensor 1 is increased in advance. The mean stress must be at least 30 MPa.

This mean stress can be applied by, for example, applying an initial stress. The fatigue damage detection sensor 1 can be preheated before mounting on the base material M by means of adhesion, welding, or other mechanical fixing means such as bolting.

Alternatively, after the fatigue damage detection sensor 1 is mounted on the base material M by adhesion, welding, or bolting, the portion of the sensor corresponding to the indicator plate 2 is linearly heated and then cooled to allow the indicator plate 2 of the fatigue damage detection sensor 1 to be contracted in order to apply the initial stress.

FIG. 6 is a schematic explanatory drawing showing this linear heating operation. For example, after the fatigue damage detection sensor 1 has been fixed to the base material M by welding fixing portions 13, the portion of the fatigue damage detection sensor 1 corresponding to the indicator plate 2 is heated in the width-wise direction (a linearly heated portion 14) and then cooled and contracted to generate an initial stress therein in order to increase the mean stress.

In addition, FIG. 7 is a schematic explanatory drawing showing the bolting operation. Bolts 16 are inserted into the indicator plate 2 in a lateral pair of bolting areas 15 (fixing portions) to fix the fatigue damage detection sensor 1 to the base material M. Long holes 17, however, are formed in one of the bolting areas to enable the level of the mean stress to be adjusted based on their positions relative to the bolts 16.

FIG. 8 is a graph showing the stress intensity factor range $\Delta K$ vs. the crack propagation rate da/dN in cases where an initial stress is and is not applied to the indicator plate 2. This graph shows that the application of the initial stress increases the mean stress to provide a linear property and allows the crack C to occur and propagate even under a small stress, whereas no crack C occurs under a small stress if the initial stress is not applied.

In this way, this indicates that a predetermined sensing accuracy and sensitivity (the stress intensity factor range $\Delta K$ and the gap propagation rate da/dN) can be obtained by setting the length H in the indicator plate 2 at an arbitrary value.

FIG. 9 is a graph showing a preheating operation for the fatigue damage detection sensor 1 and temporal changes in the temperature of the sensor, showing how the temperature of each part of the fatigue damage detection sensor 1 increases.

This preheating method employs, for example, an H-shaped steel as the base material M, adheres the fatigue damage detection sensor 1 to the center of an upper flange 18 of the H-shaped steel, places magnets 19 on the right and left to the sensor 1 to press the affixed portions 4 against the upper flange 18 with a predetermined pressure, places a preheating heater 20 between the magnets 19, and heats the center of the indicator plate 2, as shown in the figure in the graph.

The graph shows that the difference in temperature between the center of the fatigue damage detection sensor 1 and the base material M (the center of the upper flange 18) becomes almost constant (about 30° C.) after a predetermined time period.

By fixing the fatigue damage detection sensor 1 to the base material M while maintaining this constant temperature difference, the fatigue damage detection sensor 1 allows the crack C to be stably generated and propagated and detects it despite a difference from the temperature of the external environment (for example, −20° C. to +50° C.). Consequently, the sensor 1 can sense the level of fatigue damage caused to the base material M.

BRIEF DESCRIPTION OF THE DRAWINGS

FIG. 1 is a top and front views of a fatigue damage detection sensor 1 for structural materials according to an embodiment of the present invention;

FIG. 2 is a flowchart showing a procedure for mounting the fatigue damage detection sensor 1;

FIG. 3 is an enlarged view showing a fatigue pre-crack 7 portion;

FIG. 22 shows the results of fatigue crack propagation tests; and

FIG. 23 is a graph showing the level of fatigue damage and the JSSC fatigue design curve.

BEST MODE FOR CARRYING OUT THE INVENTION

The fatigue damage detection sensor for structural materials and mounting method thereof according to the present invention will be described in conjunction with several embodiments. The present invention, however, is not limited to these embodiments.

Fatigue Tests

The fatigue damage detection sensor for structural material according to this invention was subjected to fatigue tests.

Figure 4:
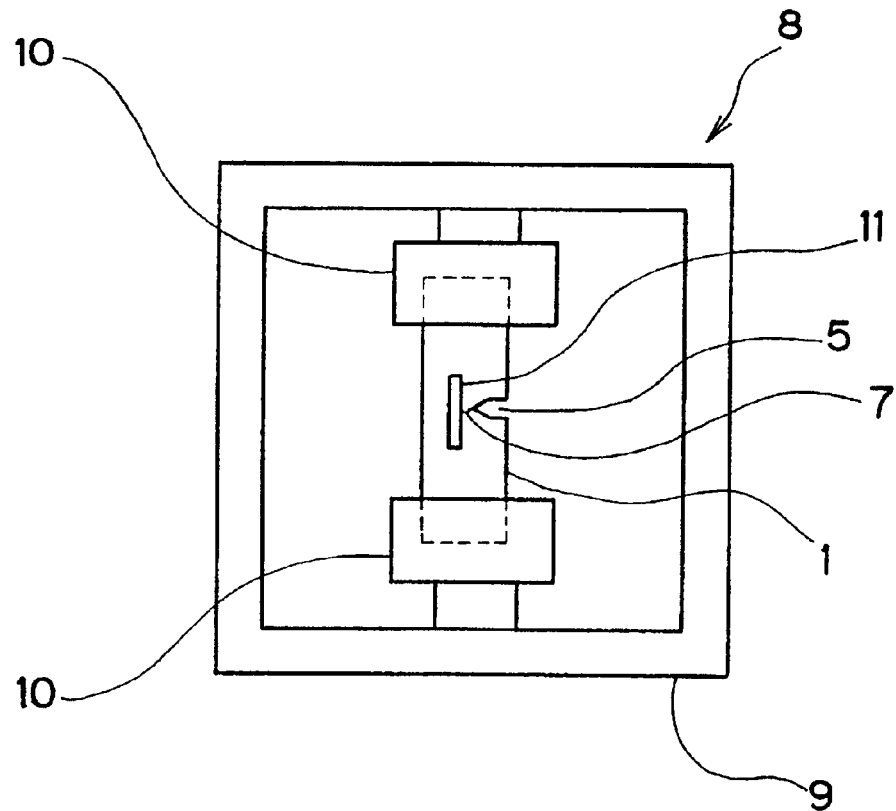
FIG. 4 is a schematic explanatory drawing of a fatigue pre-crack generator 8 for forming the fatigue pre-crack 7.
Figure 5:
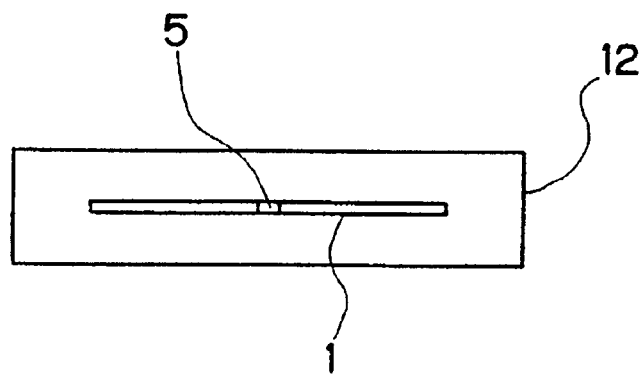
FIG. 5 is a schematic explanatory drawing describing an annealing operation in brief.
Figure 6:
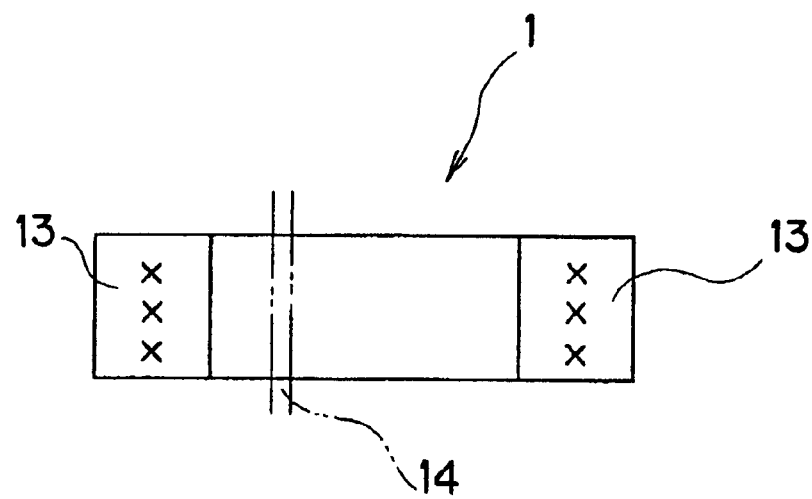
FIG. 6 is a schematic explanatory drawing showing a linear heating operation.
Figure 7:
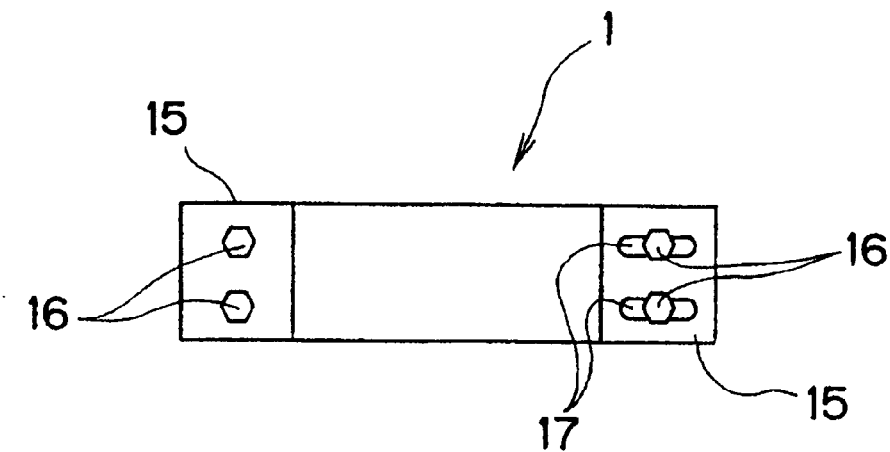
FIG. 7 is a schematic explanatory drawing showing a bolting operation.
Figure 8:
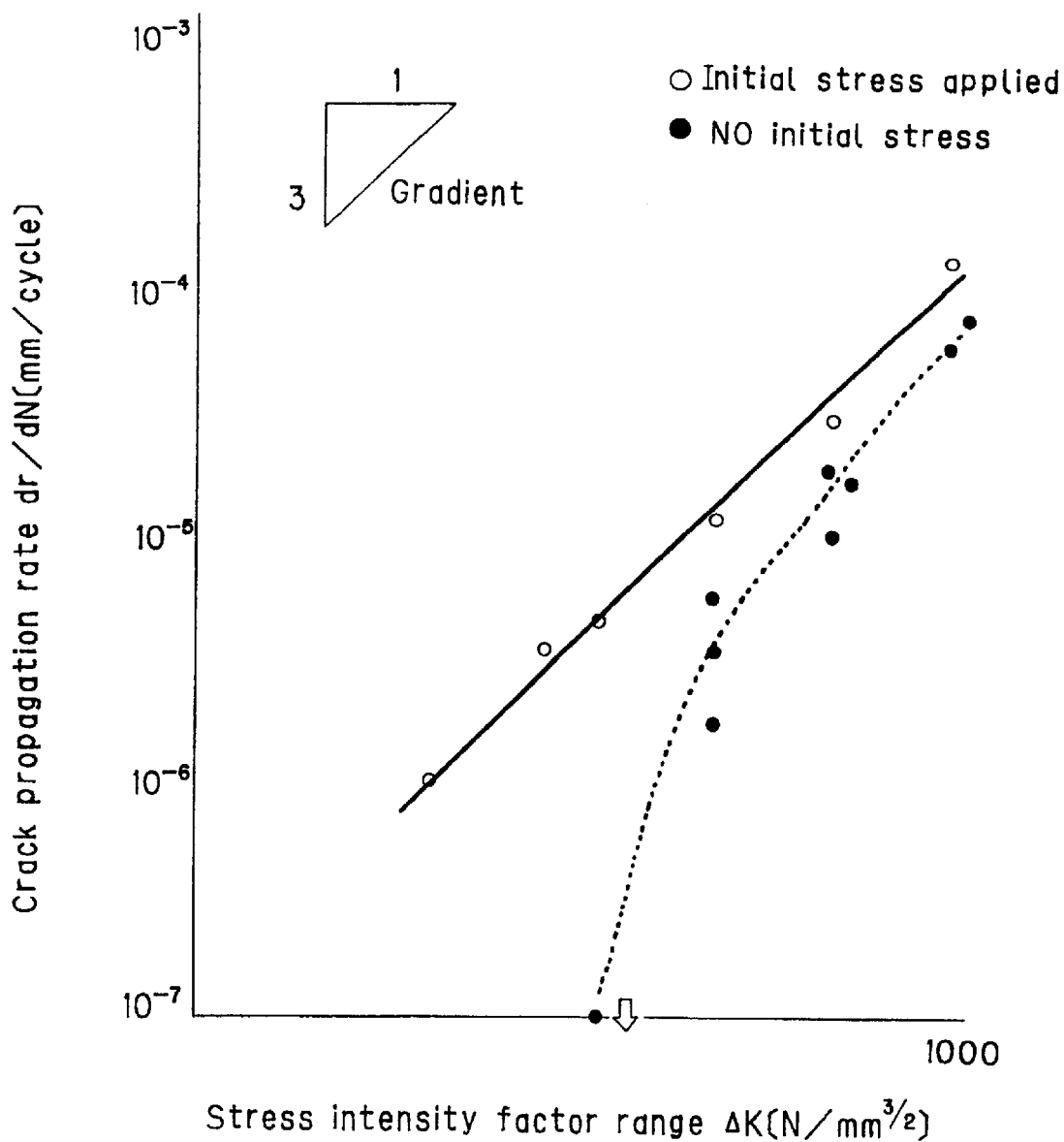
FIG. 8 is a graph showing the stress intensity factor range ΔK vs. the crack propagation rate da/dN in cases where an initial stress is and is not applied to the indicator plate 2 configured by a steel material.
Figure 9:
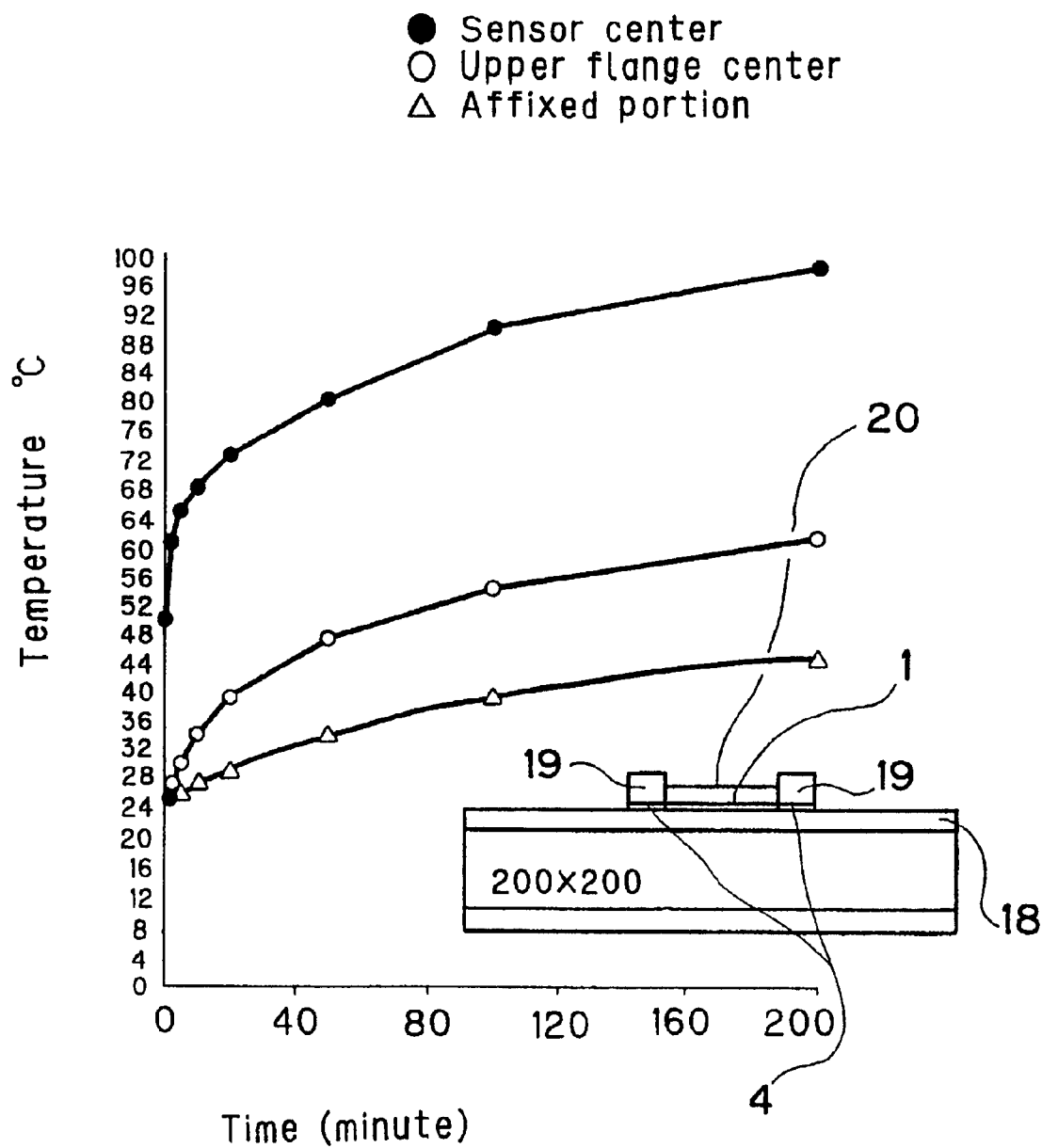
FIG. 9 is a graph showing a preheating operation for the fatigue damage detection sensor 1 and temporal changes in the temperature of the sensor.
Figure 10:
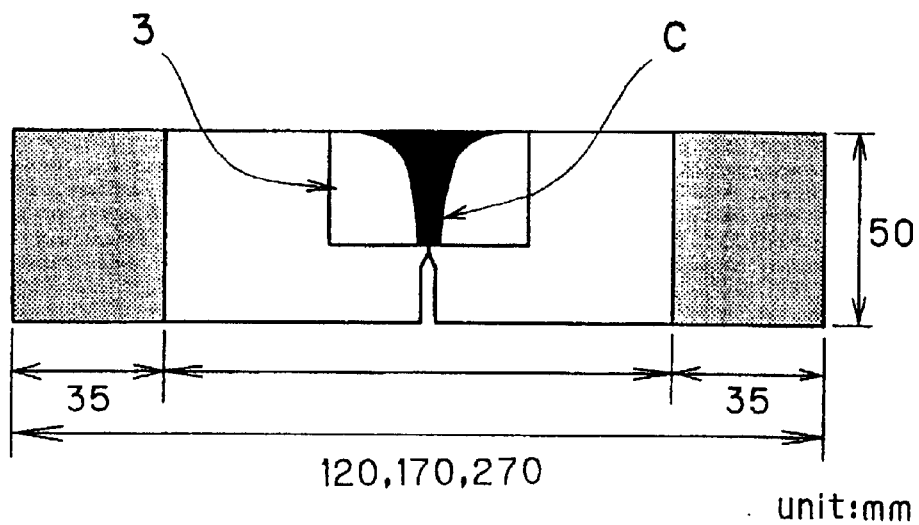
FIG. 10 is a top view of the fatigue damage detection sensor according to the embodiment.

The fatigue damage detection sensors each comprised by SUS304 and an Al—Mg alloy and had a width of 50 mm, a length of 120, 170, and 270 mm, a thickness of 0.5 and 0.3 mm, and a gauge length of 50, 100, and 200 mm (FIG. 10). The standard thickness of the sensors was 0.5 mm and the sensor of 0.3 mm thickness was used to determine the effect of the thickness.

The length of a crack was measured using a crack gauge comprising a 1-mm pitched grid and stuck to the sensor opposite to a tip of a notch portion located on its inner side.

Figure 11:
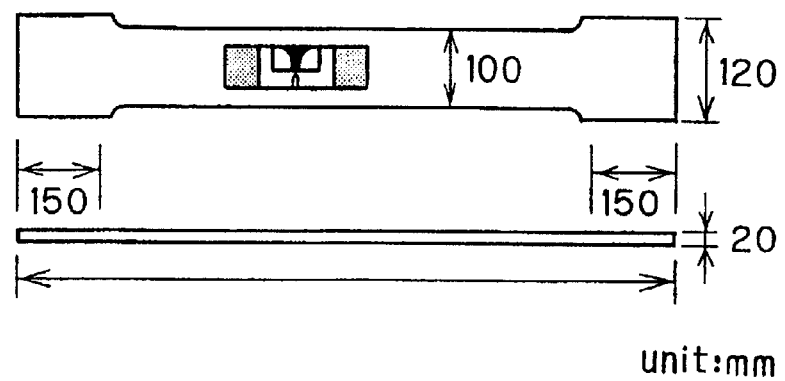
FIG. 11 is a top view of a specimen to which the fatigue damage detection sensor according to the embodiment has been affixed.

A fatigue specimen of 20 mm thickness was used for the fatigue tests (FIG. 11). The sensor was affixed to the specimen, and load controlled fatigue tests were conducted using a servo-hydraulic testing machine.

Embodiment 1

Figure 12:
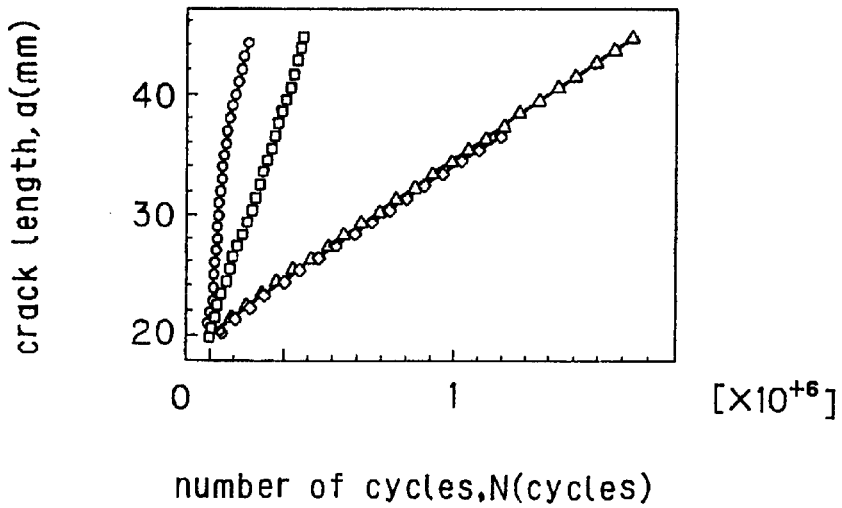
FIG. 12 is a graph showing the results of fatigue tests.

Both ends (the affixed portions in FIG. 10) of the mechanical notched sensor, that is, the above sensor were stuck to the fatigue specimen using an epoxy type adhesive, and this sensor was used to conduct the above fatigue tests under the conditions of stress range 150 MHa and stress ratio 0.1. FIG. 12 shows the results.

The results indicate that the length of a crack in the sensor was proportional to the number of stress cycles. They also indicate that the crack propagation rate does not depend on the crack length.

In addition, a comparison between the sensors of gauge length 100 mm (S100-0.5) and 50 mm (S50-0.5) indicated a significant effect of the gauge length.

The aluminum alloy (A100-0.5) appears to have a slightly higher crack propagation rate than the SUS304 (S100-0.5). Due to the softness of the aluminum alloy, however, the sensor may be damaged during handling due to an unexpected deformation. Accordingly, the SUS304 was largely used for this embodiment.

In addition, a comparison between the results on the thicknesses of 0.5 and 0.3 mm exhibited no effect of the thickness.

Figure 13:
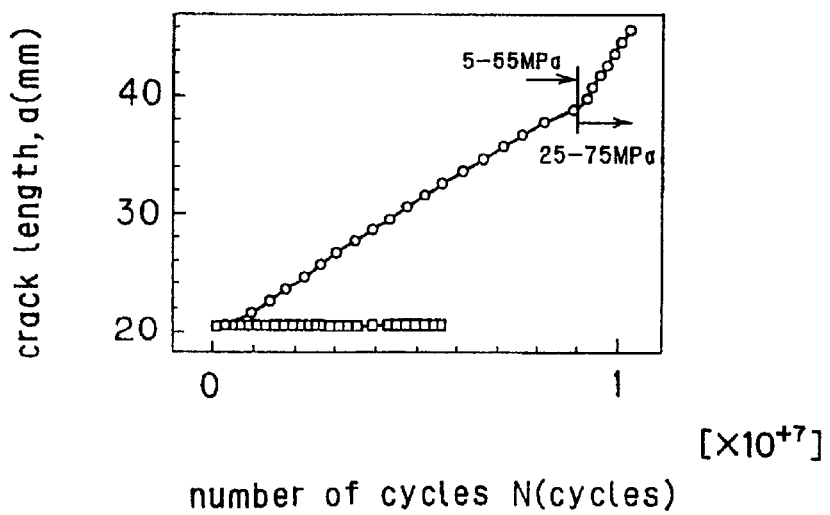
FIG. 13 is a graph showing the results of the fatigue tests.

Next, FIG. 13 shows the results of the above fatigue tests conducted under the conditions of stress range 50 MPa and stress ratio 0.1.

A crack occurred in the sensor of gauge length 200 mm, whereas no fatigue crack occurred at the tip of the mechanical notch in the sensor of gauge length 100 mm.

During the tests, when the stress ratio was changed from 0.1 to 0.33, the crack propagation rate significantly increased.

Since a stress generated in a steel structure such as a railway bridge is 50 MPa or less, a crack must be able to propagate stably even under such a low stress as about 20 or 30 MPa. A crack is expected to occur more easily from the mechanical notch tip by forming a fatigue pre-crack in the sensor and annealing the sensor to relieve the stress.

In addition, the dependency on the stress ratio observed in the fatigue tests on the sensor of gauge length 200 mm is assumed to result from a crack closure behavior. Thus, a stable crack propagation behavior is expected to be obtained by increasing the mean stress beforehand.

Embodiment 2

A fatigue pre-crack was formed in the fatigue damage detection sensor using the above method, and the sensor was annealed to relieve the stress. When affixed to the fatigue specimen, the sensor was heated to apply an initial stress thereto. When the sensor is heated, the mean stress increases after cooling due to the difference in temperature and linear expansion between the sensor of SUS304 and the fatigue specimen of steel.

Figure 14:
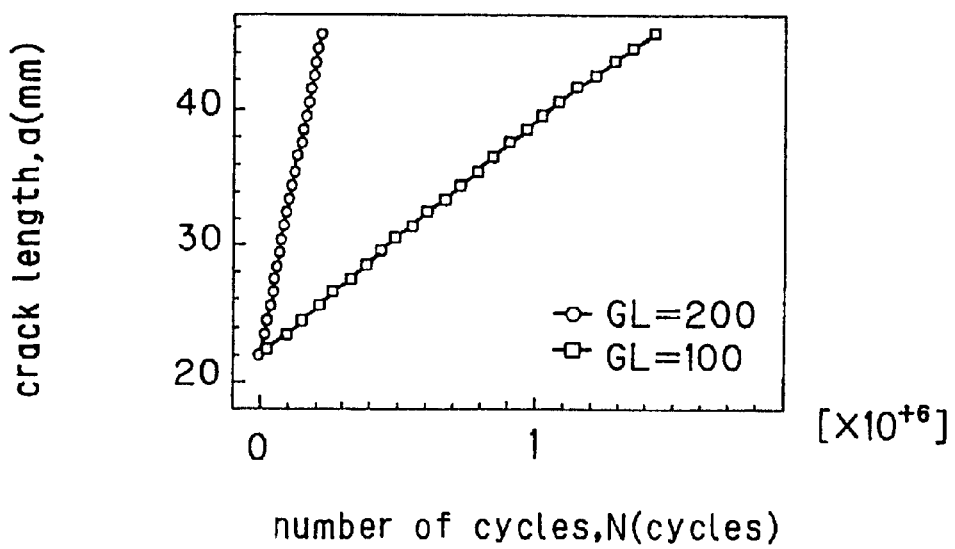
FIG. 14 is a graph showing the results of the fatigue tests.
Figure 15:
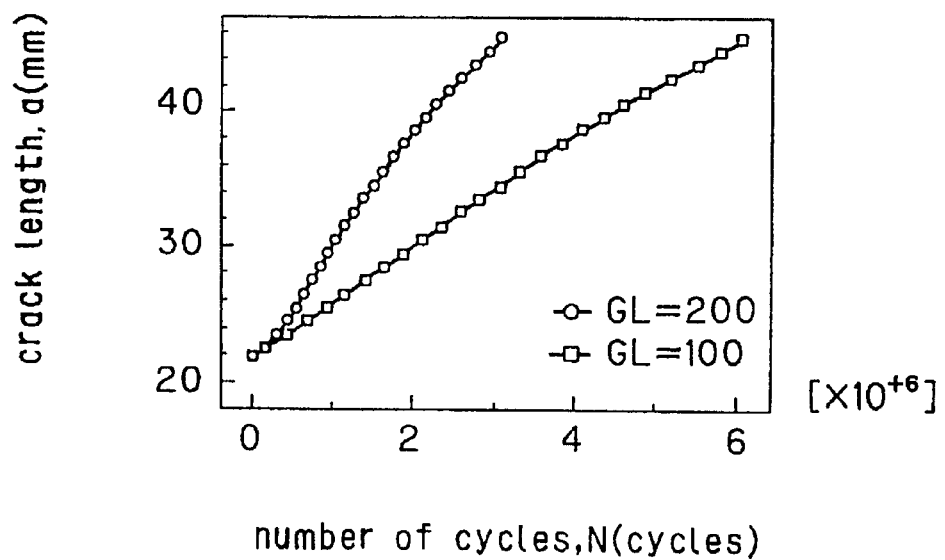
FIG. 15 is a graph showing the results of the fatigue tests.
Figure 16:
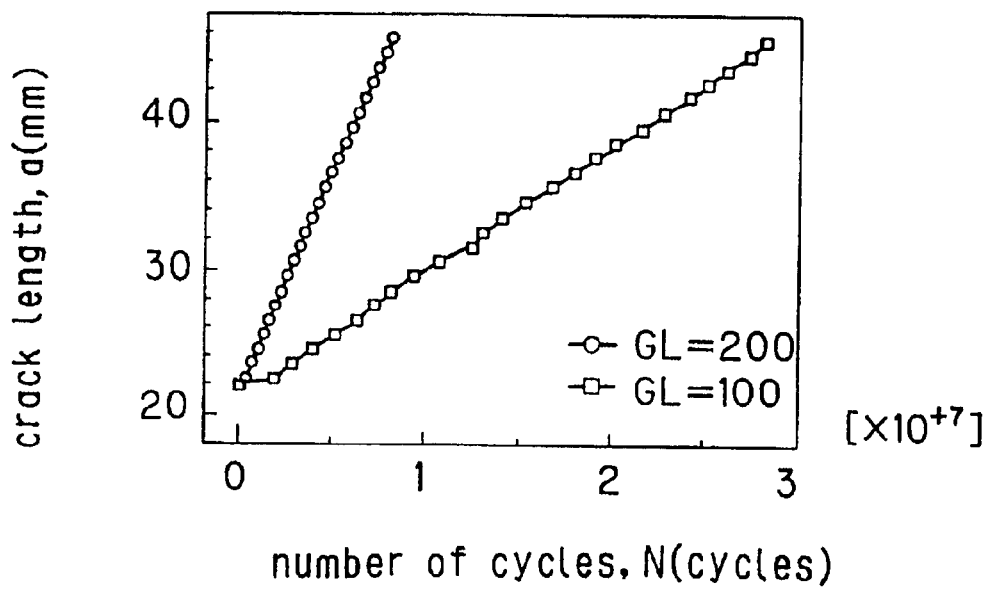
FIG. 16 is a graph showing the results of the fatigue tests.

FIGS. 14 to 16 show the results of the above fatigue tests using the sensors.

The independency of the crack propagation rate on the crack length was confirmed again.

A comparison between FIGS. 13 and 15 for the gauge length of 200 mm indicates that the crack propagation rate was significantly accelerated due to the mean stress. The crack also propagated in the sensor of 100 mm gauge length.

Besides, the crack propagated even in such a low stress range as 30 MPa and the incubation period before the crack occurred was negligibly short.

Prior to the tests, a strain gauge was stuck to the detection sensor and a released stress was measured after cracking. The measured value was −322 $\mu\epsilon$. That is, 66-MPa stress is assumed to be have been applied.

Embodiment 3

The fatigue crack was found to propagate even under a low stress range when an initial stress (pre-stress) was applied to the fatigue damage detection sensor to increase the mean stress. Thus, in order to quantitatively determine the value of a required pre-stress, the effects of the mean stress on the crack propagation properties were investigated.

Figure 18:
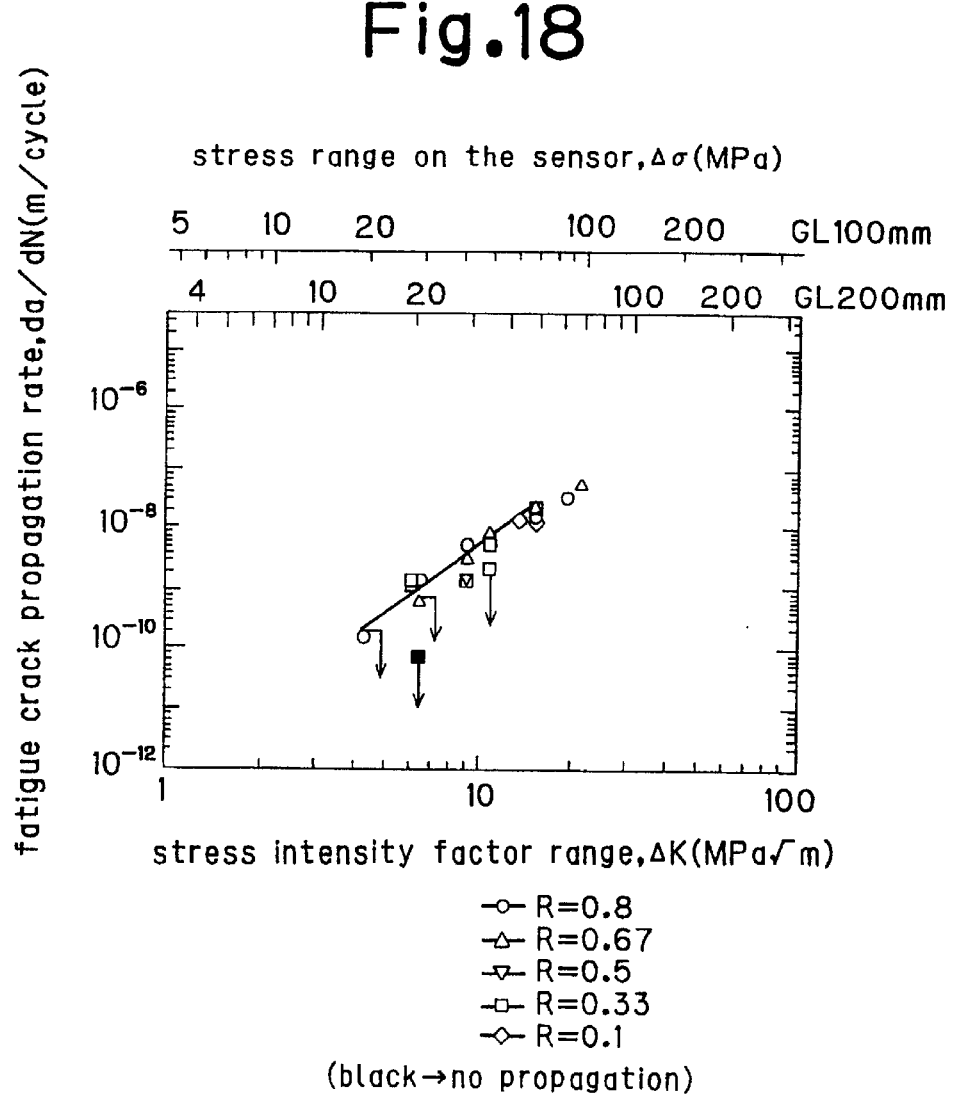
FIG. 18 is a graph showing the results of the fatigue tests.

The test was carried out under the condition that the detection sensor was stuck to the fatigue specimen without applying any pre-stress and a stress ratio was controlled by a fatigue tester. FIG. 18 shows the results.

Figure 17:
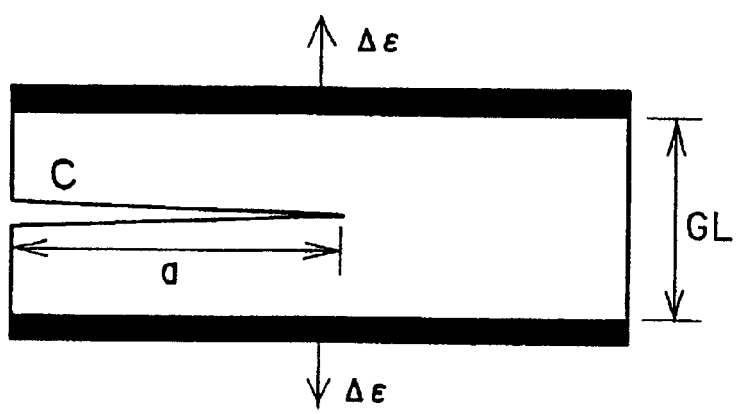
FIG. 17 is a schematic explanatory drawing showing a plate that has been subjected to a specified displacement at both ends to generate a crack on one side.

The stress intensity factor range was calculated using the following Equation (1) given for the plate having a single-sided crack (a) caused by a specified displacement $\Delta\epsilon$ (a strain variation range) applied to both ends of GL (gauge length), as shown in FIG. 17.

[Equation 1]

$$\Delta K = E \cdot \Delta\varepsilon \sqrt{GL/2} \quad (1)$$
$$= \Delta\sigma \sqrt{GL/2}$$

(in the equation, $\Delta K$ denotes the stress intensity factor range, E is denotes the modulus of longitudinal elasticity, $\Delta\epsilon$ denotes the strain variation range, GL denotes the gauge length, and $\Delta\sigma$ denotes stress).

There was a tendency that in an area where the stress intensity factor range is low, the effect of the stress ratio was significant and that the crack propagation rate decreases with decreasing stress ratio. In some of the tests, the crack did not propagate. With a stress ratio of 0.67 or more, the crack propagation rate is not affected by the stress ratio and remains stable.

Figure 19:
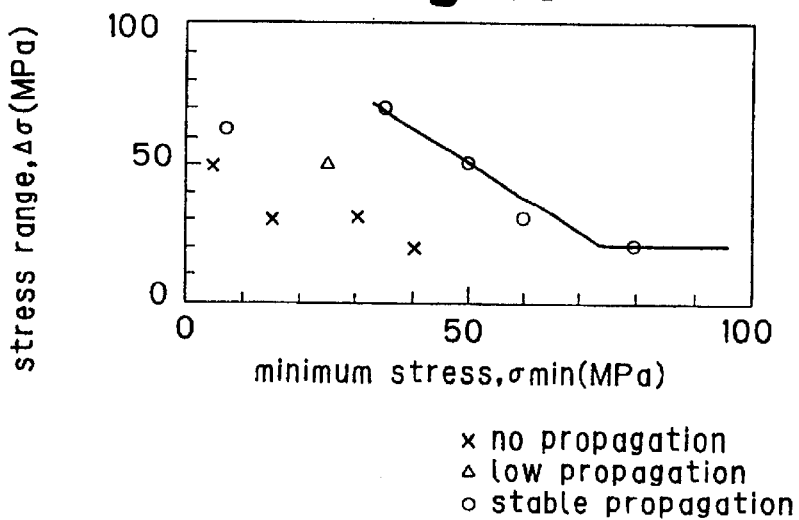
FIG. 19 is a graph showing the results of the fatigue tests.
Figure 20:
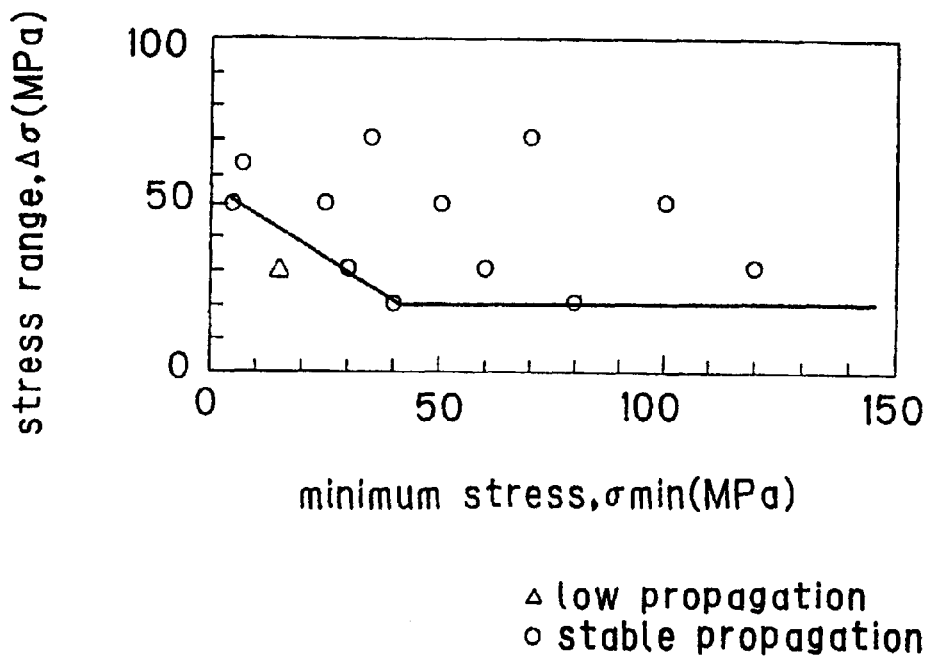
FIG. 20 is a graph showing the results of the fatigue tests.

This crack propagation rate was defined as a stable crack propagation rate, and the stress ratios were classified into those with a lower crack propagation rate and those with no crack propagation. FIGS. 19 and 20 show these results for sensors having a gauge length of 100 mm and 200 mm, respectively. The crack propagation was delayed or stopped when the minimum stress and stress amplitude were low.

An area where the crack propagated stably is shown by a solid line.

Assuming that a stress variation range to be evaluated for an actual bridge is 20 MPa or higher, it has been found that the initial stress (pre-stress) required to allow a fatigue crack in the sensor to propagate stably within this range is 70 MPa for the sensor of gauge length 100 mm and 40 MPa or more for the sensor of gauge length 200 mm.

Embodiment 4

When affixed to a structure, the fatigue damage detection sensor can be heated to introduce a pre-strain based on the difference in temperature and thermal expansion rate between the sensor and the structure. Thus, in order to provide a constantly stable pre-strain, an attempt was made to standardize the sensor affixing operation.

Figure 21:
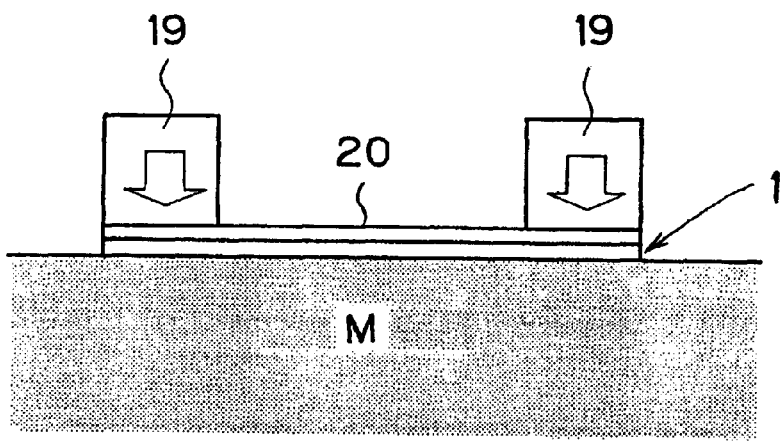
FIG. 21 is a schematic explanatory drawing describing in detail a method for affixing the fatigue damage detection sensor to a structural material.

As shown in FIG. 21, based on the method of placing a heater on the sensor and holding both ends of the heater using magnetic fixtures, conditions were determined that were required to stably introduce a 600- to 800 $\mu\epsilon$ pre-strain.

The crack propagation test was carried out under the condition that the pre-stress was applied to the fatigue damage detection sensor by the above described method.

As described above, the crack propagation rate has been confirmed to be constant irrespective of the crack length, so in this test, the stress condition was changed after a crack propagated about 5 mm. A pulsating tension having a stress ratio of 0.1 was used as a working load, and the stress range was set between 20 and 70 MPa. Due to the application of a high tensile pre-stress, the substantial stress acting on the sensor was a tension despite the use of a compression stress as a working load. Accordingly, since a crack was expected to propagate despite the use of the pulsating compression stress as a working load, a compression test using a stress ratio of 1.1 was also carried out. FIG. 22 shows the results of these tests together with the results for the stress ratio of 0.67 or more shown in FIG. 18.

The results obtained under the condition of stress ratio 0.67 or more coincide well with the results for the stress ratio of 1.1, indicating a stable crack propagation property. FIG. 22 uses a dashed line to show the crack propagation property recommended by JSSC, and the results of these tests also coincide well with this crack propagation property. In addition, to estimate the crack propagation life from given mechanical conditions, the safest design curve is commonly used that is the upper limit of the data.

However, to estimate stress history from the amount of crack propagation, the use of the lower limit provides a safer evaluation. Thus, this embodiment has used a mean design curve expressed by the following equation.

[Equation 2]

$$da/dN = 1.5 \times 10^{-11} \Delta K^{2.75} \quad (2)$$
$$da/dN : m/cycle$$
$$\Delta K : Mpa\sqrt{m}$$

(in the equation, $\Delta K$ denotes the stress intensity factor range)

Embodiment 5

The history of stress acting on a member is detected from the results of monitoring performed by the fatigue damage detection sensor according to this invention, while the level of fatigue damage is directly evaluated.

Next, a method for directly evaluating the level of fatigue damage using the fatigue damage detection sensor according to this invention will be described below.

When the crack propagation amount during a monitoring period is defined as $\Delta a$ and the working load is an equivalent stress $\Delta\sigma_{eq}$, the stress intensity factor range for the sensor is expressed by the following Expression (3) with a difference in modulus of longitudinal elasticity taken into consideration.

[Equation 3]

$$\Delta K = (197/206) \cdot \Delta\sigma_{eq} \sqrt{GL/2} \quad (3)$$

(in this equation, $\Delta K$ designates the stress intensity factor range, $\Delta\sigma_{eq}$ designates an equivalent stress, GL designates the gauge length in FIG. 10.)

From Equations (2) and (3), the following equation is derived.

[Equation 4]

$$\Delta\sigma_{eq}^{2.75} \cdot \Delta N = \frac{\Delta a}{1.5 \times 10^{-11} \{(197/206)\sqrt{GL/2}\}^{2.75}} \quad (4)$$

(in this equation, $\Delta\sigma_{eq}$ indicates an equivalent stress, $\Delta N$ indicates the number of stress cycles, $\Delta a$ indicates the amount of crack propagation, and GL indicates the gauge length in FIG. 10.)

That is, the fatigue damage $\Delta K \cdot (\Delta\sigma_{eq})^{2.75}$ can be directly sensed from the crack propagation amount of the fatigue damage detection sensor according to this invention.

FIG. 23 shows a comparison between the level of fatigue damage determined by the sensor of 200 mm gauge length (H=100 mm) and the JSSC fatigue design curves wherein the crack propagation amount $\Delta a$ is 1 or 10 mm. This figure indicates that the sensor can detect fatigue damage sufficiently early compared to the design curve F and can also be used to predict the fatigue life.

Since this sensor can detect the damage level in the form of the left side of Equation (4), the equivalent stress can be easily calculated by determining the number of stress cycles during the monitoring period.

Industrial Applicability

As described above, the present invention can obtain an arbitrary sensitivity by setting the length between the fixing portions of the detection sensor body to adjust the fatigue propagation rate and can mount the sensor on the base material (a structural material of a bridge or the like) with a predetermined stability and reliability so as to provide a predetermined sensing accuracy, using various steps including the formation of a fatigue pre-crack, the relief of a residual stress, and the mounting of the sensor with its means stress increased.

That is, the fatigue crack propagation property of the fatigue damage detection sensor according to this invention at a specified strain amplitude has been understood to establish the method for introducing a fatigue pre-crack into the sensor and annealing it for stress relief to introduce a pre-strain into it. Thus, the fatigue damage detection sensor that can operate stably under a low stress can be obtained to directly evaluate the level of fatigue damage based on the results of monitoring performed by the sensor.

What is claimed is:

1. A fatigue damage detection sensor for sensing the level of fatigue damage caused to a structural material that is subjected to a working load, the sensor comprising:
   a rectangularly configured, panel-shaped sensor body having a specified width and a pre-determined length, the sensor body including at least one notched portion which is disposed therein and defines a tip;
   a pair of fixing portions for mounting the sensor body to the structural material, the sensor body having a length 2H between the fixing portions when mounted to the structural material thereby; and
   a means for crack detection disposed on the sensor body adjacent the tip of the notched portion;
   the length 2H being set so as to cause a crack propagation rate $d(a)/dN$ to be proportional to $H^{0.5m}$, (a) being the length of a crack that propagates from the tip of the notched portion, N being the number of times that the working load acts on the structural material, H being one-half the length 2H, and m being a constant determined by the structural material.

2. The fatigue damage detection sensor of claim 1 wherein the sensor body includes a fatigue pre-crack formed therein at the tip of the notched portion.

3. The fatigue damage detection sensor of claim 1 wherein each of the fixing portions is fabricated from an adhesive.

4. A method of mounting a fatigue damage detection sensor to a structural material for sensing the level of fatigue damage caused to the structural material when the structural material is subjected to an external stress, the method comprising the steps of:
   (a) providing a rectangularly configured, panel-shaped sensor body having a specified width and a predetermined length;
   (b) forming a notched portion which defines a tip in the sensor body;
   (c) forming a fatigue pre-crack in the sensor body at the tip of the notched portion;
   (d) relieving a residual stress from the sensor body resulting from the formation of the fatigue pre-crack in step (c), the relief of the residual stress increasing a mean stress of the sensor body; and
   (e) mounting the sensor body to the structural material.

5. The method of claim 4 wherein step (e) further comprises the step of heating the sensor body prior to the mounting thereof on the structural material.

6. The method of claim 4 wherein step (e) comprises linearly heating the sensor body prior to the mounting thereof on the structural material.

7. The method of claim 4 wherein step (e) is accomplished through the use of an adhesive.

8. A method for mounting a fatigue damage detection sensor to a structural material for sensing the level of fatigue damage caused to the structural material when the structural material is subjected to an external stress, the method comprising the steps of:
   (a) providing a rectangularly configured, panel-shaped sensor body having a specified width and a predetermined length;
   (b) forming at least one notched portion which defines a tip in the sensor body;
   (c) positioning a means for crack detection on the sensor body adjacent the tip of the notched portion; and
   (d) mounting the sensor body to the structural material via a spaced pair of fixing portions such that the sensor body has a length 2H between the fixing portions, with the length 2H being set so as to cause a crack propagation rate $d(a)/dN$ to be proportional to $H^{0.5m}$, (a) being the length of a crack that propagates from the tip of the notched portion, N being the number of times that the external stress acts on the structural material, H being one-half the length 2H, and m being a constant determined by the structural material.

9. The method of claim 8 wherein step (d) comprises heating the sensor body prior to the mounting thereof on the structural material.

10. The method of claim 8 wherein step (d) comprises linearly heating the sensor body prior to the mounting thereof on the structural material.

11. The method of claim 8 wherein step (d) further comprises forming a fatigue pre-crack in the sensor body at the tip of the notched portion to relieve a residual stress in the sensor body and increase a mean stress therein.

* * * * *